United States Patent [19]

Sunada

[11] Patent Number: 4,537,573
[45] Date of Patent: Aug. 27, 1985

[54] DETECTOR FOR DIAGNOSING DENTAL CARIES

[75] Inventor: Imao Sunada, Tokyo, Japan

[73] Assignee: Noburu Onuki, Tokyo, Japan

[21] Appl. No.: 566,808

[22] Filed: Dec. 29, 1983

[51] Int. Cl.³ .............................................. A61C 3/00
[52] U.S. Cl. ...................................... 433/32; 128/735
[58] Field of Search ............................. 433/32, 27, 72; 128/735

[56] References Cited

U.S. PATENT DOCUMENTS 4,164,214  8/1979  Starh et al. ............................. 433/32
4,215,698  8/1980  Nuwayser ............................. 433/32

FOREIGN PATENT DOCUMENTS 2508742  9/1976  Fed. Rep. of Germany ...... 128/735
46-12400  3/1971  Japan .

Primary Examiner—Robert Peshock
Attorney, Agent, or Firm—Cushman, Darby & Cushman

[57] ABSTRACT

A detector for diagnosing dental caries comprising a casing capable of being grasped with one hand and housed therein a reference voltage adjusting circuit, low frequency oscillating circuit, and an amplifying circuit and voltage comparing circuit, with a tooth electrode attached to the casing, and a power switch and a plurality of indicating lamps provided on the casing, in order to improve the operation of such detectors and to enable more accurate diagnosis.

4 Claims, 7 Drawing Figures

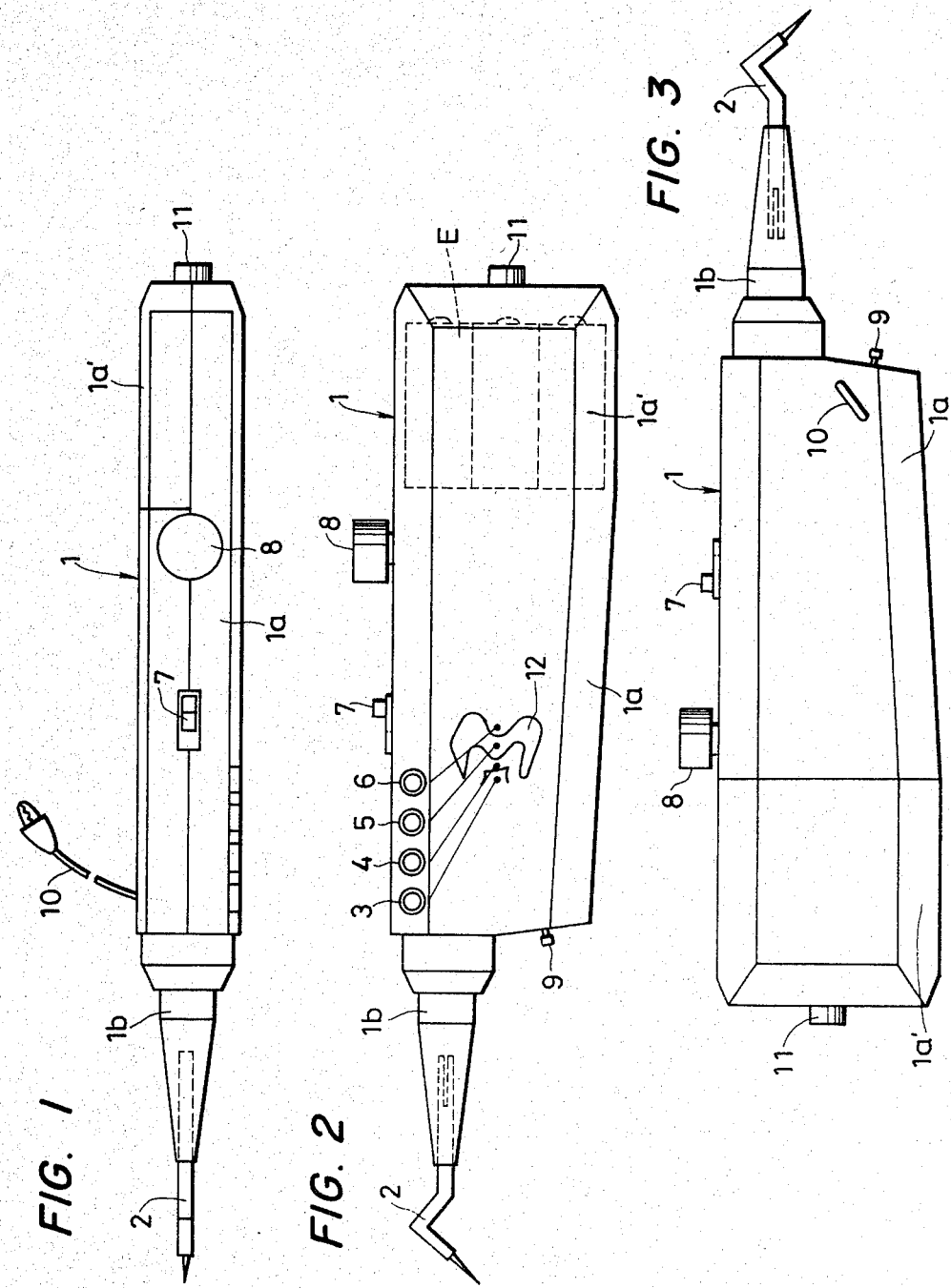

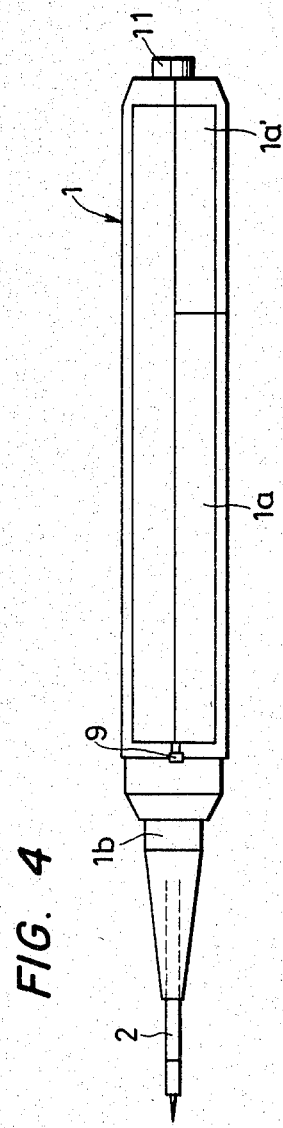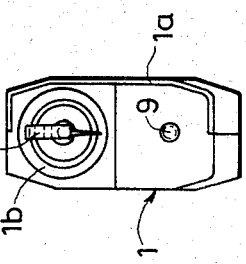
FIG. 4
FIG. 5
FIG. 6

DETECTOR FOR DIAGNOSING DENTAL CARIES

BACKGROUND OF THE INVENTION (a) Field of the Invention:

The present invention relates to a dental diagnosing device, and more particulaly, to a detector for diagnosing dental caries able to indicate the presence and progress of the dental caries with a plurality of indicating lamps classified, for example, by converting them into an electric parameter such as an electric resistance.

(b) Description of the Prior Art:

Lengthy study has shown that presence of the initial dental caries and the progress of dental caries can be diagnosed by measuring the electrical resistance between the teeth and buccal mucous membrane. Specifically, it has been shown that caries do not exist or the probability of occurrence of the caries is small when the electrical resistance shows a value more than 600Ω, or when a coloring, chalk-like variation or the like is observed on the top surface of the teeth. It is necessary to observe adequately the subsequent changes when the electrical resistance takes a value between 599∼251kΩ and the progress of the caries has arrived in the region of the dentine of the teeth, because it will become the dentine caries after 1 or 2 years almost without exception when the electrical resistance takes a value between 250∼15.1kΩ, regardless of the appearance of the teeth. In addition, the exposure of the pulp is apparently indicated when the electrical resistance takes a value less than 12kΩ, but treatment for restoring the pulp is usually judged clinically proper when the electrical resistance takes a value of less than 18kΩ.

Based upon the results of the study mentioned above, a device for diagnosing dental caries was disclosed in Japanese Patent Publication No. 46-12400 published Mar. 30, 1977 and is in practical use. The conventional device of this sort is formed with a measuring and indicating device portion comprising a tooth electrode, power switch and plurality of indicating lamps and, a measuring circuit device portion being independent of the measuring and indicating device portion and comprising a reference voltage adjusting circuit, low frequency oscillating circuit, amplifying circuit, voltage comparing circuit, and the. However, because it is used by connecting these two device portions with a cord, such problems as a disconnection of the cord, an imperfection of the connection, and the like might occur. Moreover, the conventional device is provided with only an indicating lamp which lights when the teeth resistance is more than 600kΩ, an indicating lamp which lights when the teeth resistance is between 600kΩ∼250kΩ, and an indicating lamp which lights when the teeth resistance is less than 250kΩ; thus, a user is not able to judge with these indicating lamps whether the amputation of dental pulp is necessary.

SUMMARY OF THE INVENTION

The primary object of the present invention is to provide a detector for diagnosing dental caries which is able to overcome the defects of the above-mentioned conventional device while providing at the same time the indicating accuracy of lamps and their convenience.

This object, according to the present invention, is attained by housing the measuring circuit device (which is) able to discriminate and indicate the presence and progress of the dental caries in collaboration with the indicating lamps) within a casing that is able to be grasped with one hand and has a tooth electrode and a plurality of indicating lamps.

According to a preferred embodiment of the present invention, the casing is formed as an elongate box, the tooth electrode is rotatably mounted on the front end portion of the casing, and a means to set the reference value to be applied to the measuring circuit device is provided on the casing. Thereby, the detector is able to effect the calibration just before use and can be used in a posture most suitable for operation it.

According to another preferred embodiment of the present invention, on the surface of the casing is a red indicating lamp to light when the teeth resistance is less than 18kΩ, an orange indicating lamp which lights when the teeth resistance is between 18kΩ and 250kΩ, a yellow indicating lamp which lights when the teeth resistance is between 250kΩ and 600kΩ, and a green indicating lamp which lights when the tooth resistance is more than 600kΩ. The lamps are aligned with each other to enable a visual indication of the presence and progress of the dental caries by having one of the above-mentioned indicating lamps light up. Thereby, it is able to provide a detector for diagnosing dental caries which is very easily used.

This and other objects of the present invention will become more apparent during the course of the following description and appended claims.

BRIEF DESCRIPTION OF THE DRAWINGS

FIG. 1 is a plan view of the detector for diagnosing dental caries according to the present invention;

FIG. 2 is a front view of the detector shown in FIG. 1;

FIG. 3 is a back view of the detector shown in FIG. 1;

FIG. 4 is a bottom view of the detector shown in FIG. 1;

FIG. 5 is a left side view of the detector shown in FIG. 1;

FIG. 6 is a right side view of the detector shown in FIG. 1; and

DESCRIPTION OF THE PREFERRED EMBODIMENT

Figure 7:
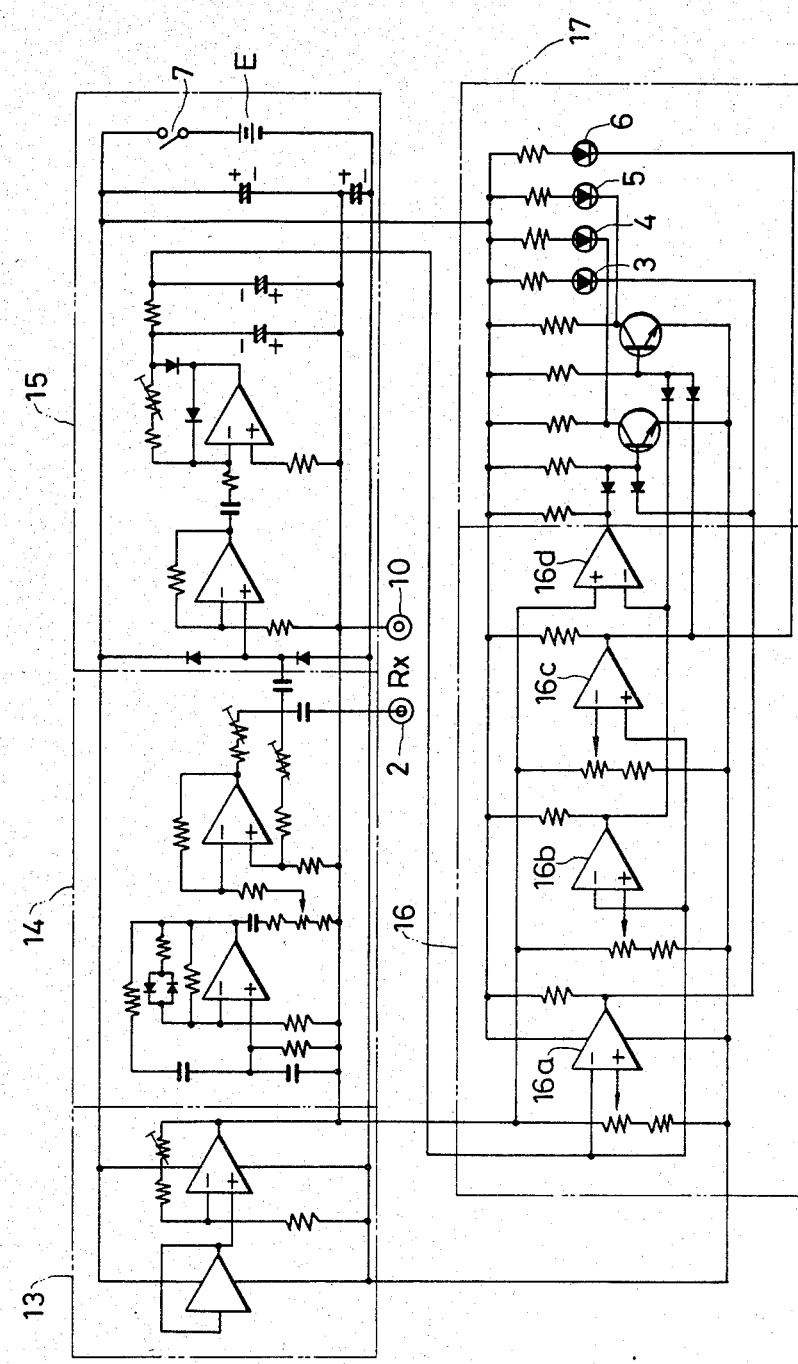
FIG. 7 is a wiring diagram to show an embodiment of the measuring circuit device portion used in the detector according to the present invention.

Referring to FIGS. 1 through 6 of the drawings, reference numeral 1 is a casing comprising an empty body portion 1a formed as a whole in a polygonal pen-like shape so as to be easily grasped with one hand and a tooth electrode fitting portion 1b, 2 is a tooth electrode formed in V-shape and fitted detachably and rotatably on the tooth electrode fitting portion 1b; 3, 4, 5, and 6 are indicating lamps such as LEDS or the like arranged on the side wall upper portion of the body portion 1a and colored, for example, in red, orange, yellow, and green, respectively 7 is a power switch attached on the top wall of the body portion 1a; 8 is a reference value adjusting knob attached on the top wall of the body portion 1a; 9 is a push button switch for adjustment which is normally opened and attached on the lower portion of the front wall of the body portion 1a; 10 is an earth clip drawn out from the side wall of the body portion 1a; 11 is a screw to fix a cover portion 1a' on the body portion 1a to house an electric source battery E within the body portion; 12 is a tooth pattern represented on the side surface of the body portion 1a so as to visually inform the progress of the dental caries in connection with the indicating lamps 3, 4, 5, and 6.

FIG. 7 shows an example of a measuring circuit portion to be housed within the body portion 1a of the casing 1. In FIG. 7, reference numeral 13 is a reference voltage generator to supply a predetermined reference voltage; 14 is a low frequency oscillator; 15 is an amplifier; 16 is a comparator so formed as to be able to turn on any one of the indicating lamps 3, 4, 5, and 6 to indicate the range of resistance valves to which the measured resistance value belongs based on a comparison between the reference voltage supplied from the reference voltage generator 13 and the voltage supplied from the amplifier 15 in response to the resistance value Rx between the tooth electrode 2 and earth clip 10 or the measured resistance value of the teeth to be diagnosed; and 17 is a lighting circuit so formed as to be able to selectively turn on the indicating lamps 3, 4, 5, and 6 by the output from the comparator 16.

The calibration of the above-mentioned measuring circuit or the setting of the reference value is effected by firstly turning on the power switch 7 and then finding out the switching over point from the orange indicating lamp 4 to the red indicating lamp 3 by means of adequately turning the reference value adjusting knob 8 while the push button switch 9 for adjustment is kept pushed on. In other words, as a result to pushing the push button 9 for adjustment, the measuring circuit shown in FIG. 7 puts a resistor of 18kΩ between the terminals 2 and 10 and the setting of the reference value is effected by adjusting a variable resistor of the comparator 16 through the reference value adjusting knob 8 so that the indicating lamp 3 lights up in that status. In addition, the comparator 16 is so formed that the indicating lamp 4 lights when the resistance value Rx to be inserted between the tooth electrode 2 and earth clip 10 is 18~250kΩ, the indicating lamp 5 lights when Rx is 250~600kΩ and the indicating lamp 6 lights when Rx is more than 600kΩ.

The detector according to the present invention as described above is operated as follows: The earth clip 10 is connected to the buccal mucous membrane (after having effected such calibration as mentioned above) and the tip end of the tooth electrode 2 is placed on the top surface of a tooth to be diagnosed by holding the casing 1 in a pen style.

In the case where the tooth resistance Rx between the terminals 2 and 10 is less than 18kΩ, a signal will be put out only by comparator 16a, causing only the red indicating lamp 3 to light; in the case where Rx is between 18kΩ and 250kΩ, a signal will be put out by comparators 16a and 16b, causing only the orange indicating lamp 4 to light; in the case where Rx is between 250kΩ and 600kΩ, a signal will be put out by comparators 16b and 16c, causing only the yellow indicating lamp 5 to light; and in the case where Rx is more than 600kΩ, a signal will be put out only by comparator 16c, causing only the green indicating lamp 6 to light. By the color difference of the indicating lamp thus lighted and the tooth patern 12 relevant thereto, the presence and progress of the dental caries can be easily and accurately diagnosed.

The indicating lamps of the above-mentioned embodiments are four which are linearly arranged but, the number of indicating lamps and the colors thereof are not limited to those of the embodiment.

I claim:

1. A detector for diagnosing dental caries comprising:
    a casing having thereon a plurality of indicating lamps, said casing being shaped so as to be easily grasped with one hand;
    a tooth electrode attached to an end portion of said casing;
    a second electrode;
    a measuring circuit means within said casing and connected to said indicating lamps, tooth electrode, and second electrode, for determining said measuring the presence and progress of dental caries and indicating such progress in cooperation with said indicating lamps;
    an adjusting means, provided on said casing and connected to said measuring circuit means, for setting a reference voltage for calibrating said measuring circuit means; and
    a tooth pattern indicia provided on said casing and associated with said indicating lamps to enable one to visually observe the progress of dental caries.

2. A detector for diagnosing dental caries according to claim 1 in which said tooth electrode is attached rotatably with respect to said casing, and said second electrode is an earth clip.

3. A detector for diagnosing dental caries according to claim 1 or 2 in which said tooth electrode has a tip portion formed in a V-shape.

4. A detector for diagnosing dental caries according to claim 1 or 2 in which said plurality of indicating lamps consist of a red indicating lamp to be lighted when teeth resistance is less than 18kΩ, an orange indicating lamp to be lighted when the teeth resistance is between 18kΩ and 250kΩ, a yellow indicating lamp to be lighted when the teeth resistance is between 250kΩ and 600kΩ and a green indicating lamp to be lighted when the teeth resistance is more than 600kΩ.

* * * * *